(12) United States Patent
Chinnari et al.

(10) Patent No.: US 12,419,867 B2
(45) Date of Patent: *Sep. 23, 2025

(54) STABLE PHARMACEUTICAL COMPOSITIONS OF BENDAMUSTINE

(71) Applicant: AZURITY PHARMACEUTICALS, INC., Woburn, MA (US)

(72) Inventors: Harish Govindaraja Setty Chinnari, Hyderabad (IN); Somashekhar Battini, Hyderabad (IN); Sumitra Ashokkumar Pillai, Hyderabad (IN); Lourdu Chinnu Thippabattuni, Hyderabad (IN); Satheesh Balasubramanian, Hyderabad (IN)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/758,225

(22) Filed: Jun. 28, 2024

(65) Prior Publication Data

US 2024/0350459 A1 Oct. 24, 2024

Related U.S. Application Data

(63) Continuation of application No. 18/502,396, filed on Nov. 6, 2023, now Pat. No. 12,208,086, which is a continuation of application No. 18/328,392, filed on Jun. 2, 2023, now Pat. No. 11,844,784, which is a continuation of application No. 17/877,476, filed on Jul. 29, 2022, now Pat. No. 11,707,450.

(30) Foreign Application Priority Data

Mar. 3, 2022 (IN) ............................ 202241011650

(51) Int. Cl.
| | | |
|---|---|---|
| A61K 31/4184 | (2006.01) | |
| A61K 9/00 | (2006.01) | |
| A61K 9/08 | (2006.01) | |
| A61K 47/02 | (2006.01) | |
| A61K 47/10 | (2017.01) | |

(52) U.S. Cl.
CPC ........ *A61K 31/4184* (2013.01); *A61K 9/0019* (2013.01); *A61K 9/08* (2013.01); *A61K 47/02* (2013.01); *A61K 47/10* (2013.01)

(58) Field of Classification Search
None
See application file for complete search history.

(56) References Cited

U.S. PATENT DOCUMENTS

| | | |
|---|---|---|
| 8,344,006 B2 | 1/2013 | Drager et al. |
| 8,609,707 B2 | 12/2013 | Palepu et al. |
| 9,603,930 B2 | 3/2017 | Patel |
| 10,010,533 B2 | 7/2018 | Palepu et al. |
| 10,052,385 B2 | 8/2018 | Sundaram |
| 11,103,483 B2 | 8/2021 | Palepu et al. |
| 2011/0190363 A1 | 8/2011 | Drager et al. |
| 2013/0210879 A1 | 8/2013 | Palepu et al. |
| 2013/0253025 A1 | 9/2013 | Sundaram |

FOREIGN PATENT DOCUMENTS

| | | |
|---|---|---|
| DE | 159289 A1 | 3/1983 |
| WO | WO 2020/035806 A1 | 2/2020 |

OTHER PUBLICATIONS

Maas, B., et al., "Stability of Bendamustine Hydrochloride in Infusion Solutions," Die Pharmazie, Govi Verlag Pharmaceutischer Verlag GMBH, vol. 49., No. 10, pp. 775-777 (1994) (English translation) (Year: 1994).

*Primary Examiner* — Adam C Milligan
*Assistant Examiner* — Jed A Kucharczk
(74) *Attorney, Agent, or Firm* — Birch, Stewart, Kolasch & Birch, LLP

(57) ABSTRACT

Stable, injectable pharmaceutical compositions are provided, which are useful as ready-to-dilute (RTD) or ready-to-use (RTU) liquid injectable compositions comprising bendamustine or a pharmaceutically acceptable salt thereof, and which are suitable for intravenous administration. Preferably, solution formulations comprise (a) bendamustine, or pharmaceutically acceptable salts, solvates, or hydrates thereof, (b) at least one pharmaceutically acceptable non-aqueous solvent; (c) optionally, at least one pharmaceutically acceptable excipient, and (d) optionally, a pH adjuster, where the pharmaceutical composition is antioxidant-free, and formulated as a ready-to-dilute or ready-to-use liquid composition suitable for parenteral administration. The invention further relates to methods for manufacturing stable, antioxidant-free injectable solutions of bendamustine.

16 Claims, No Drawings

STABLE PHARMACEUTICAL COMPOSITIONS OF BENDAMUSTINE

CROSS-REFERENCE TO RELATED APPLICATIONS

This application is a Continuation of copending application Ser. No. 18/502,396 filed on Nov. 6, 2023, which is a Continuation of application Ser. No. 18/328,392 filed on Jun. 2, 2023 (now U.S. Pat. No. 11,844,784 issued on Dec. 19, 2023), which is a Continuation of application Ser. No. 17/877,476 filed on Jul. 29, 2022 (now U.S. Pat. No. 11,707,450 issued on Jul. 25, 2023), which claims priority to Indian Application No. IN 202241011650, filed on Mar. 3, 2022, all which are incorporated herein by reference in their entirety.

FIELD OF THE INVENTION

In certain embodiments, the present invention relates to stable ready-to-dilute or ready-to-use liquid injectable compositions comprising bendamustine or a pharmaceutically acceptable salt thereof. In certain aspects, stable injectable solution formulations comprising bendamustine or pharmaceutically acceptable salts, solvates, or hydrates thereof, are provided, which are suitable for intravenous administration and free of antioxidants. Methods for manufacturing stable injectable solutions of bendamustine are also provided.

BACKGROUND OF THE INVENTION

Bendamustine hydrochloride, an alkylating drug, is a benzimidazole analog. Bendamustine was initially synthesized in 1963 in the German Democratic Republic (GDR) and was available for use, from 1971 to 1992 under the trade name CYTOSTASAN®. Since that time, it has been marketed in Germany under the trade name RIBOMUSTIN®. The chemical name of bendamustine hydrochloride is 1H-benzimidazole-2-butanoic acid, 5-[bis(2-chloroethyl)amino]-1-methyl-, mono-hydrochloride. Bendamustine hydrochloride contains a mechlorethamine group and a benzimidazole heterocyclic ring with a butyric acid substituent, and has the following structural formula:

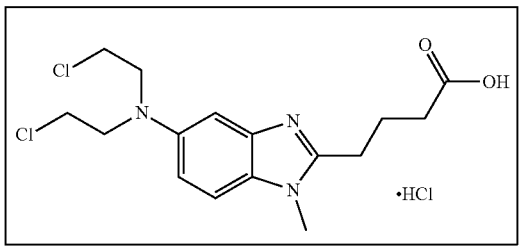 [SMILES: Cn1c(CCCC(=O)O)nc2cc(N(CCCl)CCCl)ccc21 ; Cl]

Bendamustine hydrochloride is currently approved and marketed in the United States under the brand names TREANDA®, BENDEKA® and BELRAPZO® for the treatment of non-Hodgkin's lymphoma and chronic lymphocytic leukemia.

Bendamustine hydrochloride undergoes hydrolysis rapidly in aqueous solution by direct substitution rather than an addition elimination process due to the presence of the highly labile aliphatic chlorine atoms. Bendamustine also undergoes photolytic and oxidative degradation. Some of the bendamustine degradants are Dihydroxy compound, Mono-substituted (MS) impurity, Mono-chloro (MC) impurity and Ethyl Ester (EE) impurity. To avoid rapid hydrolytic degradation of bendamustine during long-term storage, lyophilization or non-aqueous solvent system techniques were used to formulate bendamustine pharmaceutical compositions.

TREANDA® lyophilized powder for IV infusion is supplied as a sterile non-pyrogenic lyophilized powder in a single-dose vial in 100 mg and 25 mg strengths. Each lyophilized vial contains bendamustine hydrochloride and mannitol. Lyophilized powder should be reconstituted with only Sterile Water for Injection, wherein the reconstituted solution has a pH of 2.5-3.5. The reconstituted solution must be transferred to the 500 mL infusion bag of 0.9% sodium chloride Injection, USP or 2.5% Dextrose/0.45% sodium chloride injection. The resulting final concentration of bendamustine HCl in the infusion bag should be within 0.2 to 0.6 mg/mL.

The freeze-dried injections currently in use are prepared in the form of powder due to the instability of the drug in aqueous solution and reconstituted with physiological saline or water for injection before administration to the patient. However, this reconstitution process is troublesome, there is a risk of microbial contamination in the reconstitution process, and there is a limit to be used within a certain time after reconstitution. Such a lyophilized formulation may take a long time due to a long drying cycle in the lyophilization process, resulting in an increase in production cost and complicated manufacturing process. In view of economical efficiency at the time of manufacturing, ease of use, and the like, there is a need for a ready-to-use or ready-to-dilute liquid composition with stability.

German Patent No. 159289 discloses ready-to-use injectable solution of bendamustine in 1,2-propylene glycol or ethanol.

U.S. Pat. No. 8,344,006 discloses liquid formulations comprising bendamustine in polar aprotic solvents like dimethylacetamide.

Currently, liquid formulations of bendamustine are approved and sold in the U.S. under brand names BENDEKA® and BELRAPZO®. Both BENDEKA® and BELRAPZO® products contains 100 mg/4 mL solution of bendamustine hydrochloride which needs to be diluted before use. Each milliliter contains 25 mg of bendamustine hydrochloride, 0.1 mL of propylene glycol, USP, 5 mg of monothioglycerol, NF, in polyethylene glycol 400, NF. Sodium hydroxide may be used to adjust the acidity of polyethylene glycol 400.

BENDEKA® must be diluted before administration by transferring a concentrate solution to 50 mL of diluents such as 0.9% sodium chloride Injection, USP or 2.5% Dextrose/0.45% sodium chloride injection or 5% Dextrose injection, USP. The resulting final concentration of bendamustine HCL in the infusion bag should be within 0.49 mg/mL to 5.6 mg/mL. The recommended dose to treat Chronic Lymphocytic Leukemia (CLL) is 100 mg/m² administered intravenously over 10 minutes on Days 1 and 2 of a 28-day cycle, up to 6 cycles. The recommended dose to treat Non-Hodgkin Lymphoma (NHL) is 120 mg/m² administered intravenously over 10 minutes on Days 1 and 2 of a 21-day cycle, up to 8 cycles. Adverse reactions of any grade that occurred with a frequency greater than 5% during BENDEKA® infusion and within 1 hour post-infusion were nausea (8.2%) and fatigue (5.5%).

Bendamustine hydrochloride undergoes photolytic, oxidative and hydrolytic degradation rapidly in solutions. Hence, all commercially available injectable solutions of bendamustine hydrochloride should be stored at 2 to 8° C. to retard loss of potency. Therefore, inhibiting bendamustine hydrochloride degradation is of significance both clinically and from preventing significant loss of potency.

In order to protect bendamustine against oxidative degradation, a common method is to add an antioxidant to the formulation. Although antioxidants are used to stabilize solutions of bendamustine which is highly susceptible to oxidation, these excipients such as antioxidants and other excipients like amines, amino acids, solubilizers, complexing agents etc. qualify as extraneous agents and must be avoided if possible. The health authorities all over the world are very concerned about the level of such extraneous agents in the pharmaceutical compositions, particularly those meant for injectable/parenteral use. It is more desirable to avoid these agents for compositions comprising anti-neoplastic drugs like bendamustine, since patients undergoing chemotherapy, who are already facing severe side effects of the anti-neoplastic drug, cannot tolerate even a slight increase in the side effect which these extraneous agents may cause. Avoiding these excipients and still achieving an injectable solution of bendamustine that have long term stability is a challenge and an unmet need.

An infusion reaction is a type of hypersensitivity reaction that develops during administration or shortly after administration of a drug. Signs and symptoms may include pruritus, urticaria, fever, rigors/chills, diaphoresis, bronchospasms, and cardiovascular collapse. Although infusion related reactions make up a small percentage of adverse drug reactions, they still carry a significant economic impact. Infusion-related reactions may lead to prolonged infusion times, reduced drug concentration, dose reductions, dose delays, and/or discontinuation of the drug. They also can lead to hospitalizations and compromise optimal cancer therapy outcome. For this reason, it is important for all oncologists, nurses, and pharmacists to have a fundamental background in the prevention and management of infusion reactions.

The U.S. FDA adverse event reporting system shows several cases collectively related to infusion site reactions (e.g., pain, reaction, irritation & extravasation) and infusion related reactions when patients were administered with BENDEKA®. These infusion site reactions or infusion related reactions may be attributed to rapid infusion (over 10 minutes) of bendamustine at high concentration (ranging from 0.49 mg/ml to 5.6 mg/mL).

BELRAPZOR must be diluted before administration by transferring concentrate solution to 500 mL of diluents such as 0.9% sodium chloride Injection, USP or 2.5% Dextrose/ 0.45% sodium chloride injection. The resulting final concentration of bendamustine HCl in the infusion bag should be within 0.05 to 0.7 mg/mL. The recommended dose to treat Chronic Lymphocytic Leukemia (CLL) is 100 mg/m$^2$ administered intravenously over 30 minutes on Days 1 and 2 of a 28-day cycle, up to 6 cycles. The recommended dose to treat Non-Hodgkin Lymphoma (NHL) is 120 mg/m$^2$ administered intravenously over 60 minutes on Days 1 and 2 of a 21-day cycle, up to 8 cycles.

U.S. Pat. No. 8,609,707 discloses usage of antioxidants such as lipoic acid, thioglycerol (also known as monothioglycerol), propyl gallate, methionine, cysteine, metabisulfites, sodium formaldehyde sulfoxylate, dihydrolipoic acid and mixtures thereof for enhancing stability of bendamustine liquid compositions.

As mentioned above, solutions of bendamustine are prone to oxidation either by exposure to oxygen in the unfilled area of a container carrying the drug solution (headspace) or by the absorption of gaseous oxygen (dissolved oxygen) into the drug solution.

There is a need for improved formulations of bendamustine, which are stable.

SUMMARY OF THE INVENTION

The present invention relates to stable, liquid injectable pharmaceutical compositions comprising bendamustine or its pharmaceutically acceptable salts, solvates, hydrates thereof, and method for preparing such compositions. Preferably, the compositions are antioxidant-free, while having enhanced stability with less impurities upon storage.

In certain aspects, the invention provides a method of preparing a unit dose system in a sealed vessel comprising solutions of bendamustine having less dissolved oxygen levels in the solutions in order to obtain long-term storage stable solutions of bendamustine. In another aspect, the invention prevents or reduces the number of infusion-related adverse events by providing inventive dosage regimen to the subject by administering liquid pharmaceutical compositions of bendamustine as infusions at volumes of less than or about 250 mL over a period of about 20 minutes or less. In yet other aspects, the invention provides stable, antioxidant-free, ready-to-dilute or ready-to-use, liquid pharmaceutical compositions of bendamustine suitable for parenteral administration having enhanced stability with less impurities.

Preferably, a stable injectable pharmaceutical composition comprises, consists of, or consists essentially of: (a) a therapeutically effective amount of bendamustine or a pharmaceutically acceptable salt thereof; (b) at least one pharmaceutically acceptable non-aqueous solvent; (c) optionally, at least one pharmaceutically acceptable excipient, and (d) optionally, a pH adjuster, wherein the pharmaceutical composition is antioxidant-free, and formulated as a ready-to-dilute liquid composition suitable for parenteral administration.

An aspect of the present invention relates to stable injectable liquid composition of bendamustine hydrochloride and methods for preparing such composition, wherein the composition is antioxidant-free.

An aspect of the present invention relates to stable injectable liquid composition of bendamustine hydrochloride and methods for preparing such composition, wherein the composition is antioxidant-free and the dissolved oxygen content is less than 2 ppm.

An aspect of the present invention relates to stable injectable liquid compositions of bendamustine hydrochloride and methods for preparing such compositions, wherein the composition is antioxidant-free and total water content is not more than 2% w/w.

An aspect of the present invention relates to stable injectable liquid composition of bendamustine hydrochloride and methods for preparing such composition, wherein the composition is antioxidant free.

Advantageously, it is not necessary to control the level of head space oxygen in the container by purging inert gas. In such aspect, the vial may be filled and sealed in an inert environment, but the level of head space oxygen in the container does not need to be controlled by purging inert gas, which simplifies operations.

An aspect of the present invention relates to stable, antioxidant-free, injectable ready-to-dilute liquid compositions suitable for parenteral administration comprises (a) therapeutically effective amount of bendamustine hydrochloride; (b) one or more pharmaceutically acceptable non-aqueous solvents; and (c) one or more pharmaceutically acceptable excipients, wherein the level of mono-substituted impurity in said compositions is not more than 3.5% w/w when stored at 2-8° C. for 6 months as measured by HPLC.

In certain aspects, the inventive pharmaceutical compositions are suitable for intravenous administration.

The inventive compositions are advantageously ready-to-use (RTU) or ready-to-dilute (RTD) formulations. An aspect of the invention relates to stable ready-to-use or ready-to-dilute bendamustine hydrochloride compositions suitable for parenteral administration, wherein the compositions are antioxidant-free.

An aspect of the present invention relates to method of treating chronic lymphocytic leukemia or indolent B-cell non-Hodgkin's lymphoma in a subject in need of treatment comprising: parenterally administering to the subject, over a period of less than or equal to about 20 minutes, about 250 mL or less of a liquid composition comprising: bendamustine or a pharmaceutically acceptable salt thereof, at least one non-aqueous solvent, a parenterally acceptable diluent, wherein the liquid composition is antioxidant-free.

The inventive bendamustine hydrochloride containing compositions are administered as intravenous infusions at volumes of about 50 mL or about 250 mL or about 500 mL over a time period of about 10 minutes or about 20 minutes or about 60 minutes respectively.

An aspect of the present invention covers stable, ready-to-dilute, antioxidant-free, liquid compositions of bendamustine or its pharmaceutically acceptable salts, solvates, hydrates thereof, suitable for parenteral administration.

In an aspect, the present invention provides stable, antioxidant-free, injectable compositions comprising bendamustine and at least one pharmaceutically acceptable non-aqueous solvent. Regardless of the pharmaceutically acceptable non-aqueous solvent included, the amount of bendamustine included in the composition ranges from about 10 mg/mL to about 100 mg/mL, preferably 25 mg/mL.

In another aspect, the present invention provides stable, antioxidant-free, ready-to-dilute liquid compositions comprising a) bendamustine or a pharmaceutically accept able salt thereof, and b) at least one pharmaceutically acceptable non-aqueous solvent; and c) an organic compound or inorganic compound, or mixtures thereof, wherein said composition is stable for at least 6 months when stored at 2-8° C.

In another aspect, the present invention provides stable, antioxidant-free, ready-to-dilute liquid compositions comprising a) bendamustine or a pharmaceutically accept able salt thereof, and b) a pharmaceutically acceptable non-aqueous solvent; wherein said pharmaceutically acceptable non-aqueous solvent comprising polyethylene glycol (PEG) and dehydrated alcohol; wherein the pH of polyethylene glycol ranges from about 6.0 to about 11, as measured per USP official monograph methods.

In an aspect, the present invention provides stable, antioxidant-free, ready-to-dilute liquid compositions comprising: a) bendamustine; b) at least one pharmaceutically acceptable non-aqueous solvent; and c) at least one pH-adjusting agent, wherein the composition has a pH in the range of about 2 to about 5.

In certain aspects, the present invention relates to a method of preparing an injectable composition comprising following steps: (i) neutralizing polyethylene glycol (PEG) to a required pH using sodium hydroxide solution; (ii) adding dehydrated alcohol and bendamustine separately or simultaneously to neutralized polyethylene glycol (PEG) and stirring to form a clear bulk solution; (iii) adjusting pH of bulk solution to required pH; (iv) purging the nitrogen gas throughout the procedure; (v) filtering the final solution; (vi) filling the final solution in vials and stoppering with stoppers.

Each aspect above may further have one or more of the following additional elements in any combination:

Element 1: wherein the bendamustine is bendamustine hydrochloride.

Element 2: wherein a level of total impurities in said composition is not more than 5% w/w when stored at a temperature from about 2° C. to about 8° C. for 6 months as measured by HPLC.

Element 3: wherein a level of mono-substituted impurity in said composition is not more than 3.5% w/w when stored at a temperature from about 2° C. to about 8° C. for 6 months as measured by HPLC.

Element 4: wherein the level of head space oxygen in the container is not controlled by purging an inert gas.

Element 5: wherein the level of head space oxygen in the container, in which said composition is stored, is not more than 18% v/v when stored at a temperature from about 2° C. to about 8° C. for 6 months.

Element 6: wherein the level of dissolved oxygen in the composition is less than 2 ppm.

Element 7: wherein the composition has a pH from about 2.0 to about 4, preferably a pH from about 2.7 to about 3.7, most preferably a pH of about 3.5.

Element 8: wherein the at least one pharmaceutically acceptable non-aqueous solvent is selected from the group consisting of alcohol, ethanol, glycerine, polyethylene glycol (PEG), dimethylacetamide, N-methyl-pyrrolidone, dimethyl sulfoxide, and mixtures thereof. Preferably, the at least one pharmaceutically acceptable non-aqueous solvent comprises a mixture of dehydrated alcohol and polyethylene glycol (PEG), e.g., about 2-25% w/w dehydrated alcohol and about 75-98% w/w polyethylene glycol (PEG), preferably about 2-5% w/w dehydrated alcohol and about 90-98% w/w polyethylene glycol (PEG), most preferably about 3.5% w/w dehydrated alcohol and about 94% w/w polyethylene glycol (PEG).

Element 9: wherein the polyethylene glycol (PEG) is PEG-400. Preferably, the polyethylene glycol (PEG) has a pH from about 6.0 to about 11.

Element 10: wherein the pH adjuster is present, and is selected from the group consisting of sodium hydroxide, potassium hydroxide, magnesium hydroxide, sodium carbonate, tromethamine, sodium linoleate, sodium oleate, potassium carbonate, potassium linoleate, potassium oleate, and mixtures thereof. For instance, the pH adjuster comprises sodium hydroxide in an amount less than 0.5 mg/mL.

Element 11: wherein the composition comprises about 10 mg/mL to about 100 mg/mL of bendamustine or a pharmaceutically acceptable salt thereof, preferably about 20 mg/mL to about 60 mg/ml of bendamustine or a pharmaceutically acceptable salt thereof, and most preferably about 25 mg/ml of bendamustine or a pharmaceutically acceptable salt thereof.

Element 12: a method for treating chronic lymphocytic leukemia or indolent B cell non-Hodgkin's lymphoma comprising parenterally administering to a patient in need thereof a therapeutically effective amount of the stable injectable pharmaceutical composition described herein. In one aspect, the method for treating chronic lymphocytic leukemia or indolent B cell non-Hodgkin's lymphoma comprises parenterally administering to a patient in need thereof a therapeutically effective amount of a ready-to-use liquid composition having a volume of about 250 mL or less, comprising: a) about 0.05 mg/mL to about 1.36 mg/ml of bendamustine; b) at least one non-aqueous solvent; c) a parenterally acceptable diluent and (d) optionally, a pH adjuster; over a period of less than or equal to about 20 minutes. Preferably, the composition is antioxidant-free.

By way of non-limiting example, exemplary combinations applicable to the embodiments described in this application may include any combination with one or more of the elements described above. While compositions and methods are described herein in terms of "comprising" various components or steps, the compositions and methods can also "consist essentially of" or "consist of" the various components and steps.

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail. Unless specified otherwise, all the percentages, portions and ratios in the present invention are on weight basis.

As used herein, "a," "an," "the," "at least one," and "one or more" are used interchangeably. As used herein, the term "or" is generally employed in its usual sense including "and/or" unless the content clearly dictates otherwise.

As used herein the term "bendamustine" refers to bendamustine free base or its pharmaceutically acceptable salts, solvates or hydrates thereof, preferably bendamustine hydrochloride.

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to bendamustine salts which are formed with inorganic or organic acids.

The term "ready-to-use" or "RTU" as used herein refers to injectable compositions that are stable and does not require any reconstitution or dilution with parenterally acceptable diluents and can be directly administered to the patient.

Within the context of the present invention, the term "ready-to-dilute" or "RTD" as used herein refers to injectable compositions that are stable and requires reconstitution or dilution with parenterally acceptable diluents before parenteral administration.

The terms "composition", "pharmaceutical composition", "pharmaceutical product", "dosage form", "pharmaceutical dosage form", "injectable solution", "formulation", "pharmaceutical formulation", etc., refer to a pharmaceutical composition that may be administered to a patient in need of treatment, which may be in any conventional formulation. For example, the term "pharmaceutical composition" as used herein refers to a solution for parenteral administration.

The term "pharmaceutically acceptable non-aqueous solvent" refers to liquids which are substantially anhydrous, for example alcohols, polyethylene glycols, glycerol and combinations thereof.

The term "pharmaceutically acceptable excipient", as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent.

The term "therapeutically effective amount," as used herein, refers to a sufficient amount of an agent or a compound being administered which will relieve to some extent one or more symptoms of Chronic lymphocytic leukemia (CLL) or Indolent B-cell non-Hodgkin lymphoma (NHL). The result can be reduction and/or alleviation of the signs, symptoms, or causes of Chronic lymphocytic leukemia (CLL) or Indolent B-cell non-Hodgkin lymphoma (NHL), or any other desired alteration of a biological system. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effective amount" or "a therapeutically effective amount" can vary from subject to subject, due to variation in metabolism of bendamustine, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. For administration to animal or human subjects, the pharmaceutical compositions comprise an effective dosage amount of bendamustine or a pharmaceutically acceptable salt thereof, for example, depending on the subject to be treated, the mode of administration, and the type of treatment desired (e.g., prevention, prophylaxis, or therapy).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

The terms "antioxidant-free" or "free of antioxidant" as used herein, can be used interchangeably.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or colour. The term "stable" indicates both chemical and physical stability.

The term "degradation product," as used herein, refers to an unwanted chemical or impurity (including, but not limited to known or unknown related substances) that can develop during the manufacturing, transportation, and storage of drug products and can affect the efficacy of pharmaceutical products. It can form in response to changes in light, temperature, pH, and humidity, or due to inherent characteristics of active ingredient, such as their reaction with excipients or on contact with the packaging.

For purposes of the present invention, "substantially free of impurities" shall be understood to include bendamustine-containing compositions in which the amount of total impurities is less than about 10% as calculated on a normalized peak area response ("PAR") basis as determined by high performance liquid chromatography ("HPLC") at a wavelength of 235 nm, at least for a period of about 6 months at a temperature of from about 2-8° C. The quantity of impurities was further calculated based upon the original amount of bendamustine (or salt thereof) present in the composition or formulation.

For purposes of the present invention, "dehydrated alcohol" shall be understood to include an alcohol with a very low water content, e.g., an alcohol with a purity of at least 99.5% and typically a moisture level of under 0.2%, preferably a moisture level of under 0.1%, most preferably a moisture level of under 0.01%.

As used herein, RRT is calculated by dividing the retention time of the peak of interest by the retention time of the main peak. Any peak with an RRT<1 elutes before the main peak, and any peak with an RRT>1 elutes after the main peak.

In some embodiments, the amount of time the inventive compositions demonstrate long term storage stability is at least about 6 months, at least about 12 months, at least about 18 months, at least about 24 months or at least about 32 months when stored under the conditions described herein (i.e., 2-8° C.; 25° C./60% RH & 40° C./75% RH).

As used herein the term "MS" or "Mono-substituted impurities" refers to 4-(5-(2-chloroethylamino)-1-methyl-1H-benzo[d]imidazol-2yl) butanoic acid. The structure of MS is provided below:

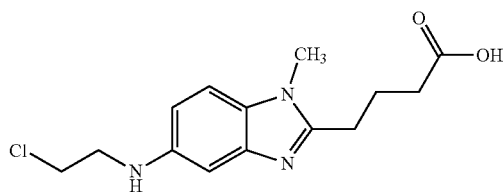 [SMILES: Cn1c(CCCC(=O)O)nc2cc(NCCCl)ccc21]

As used herein the term "MC" or "Mono-chloro impurities" refers to 4-(5-((2-chloroethyl)(2-hydroxyethyl)amino)-1-methyl-1H benzo[d]imidazol-2-yl)butanoic acid. The structure of MC is provided below:

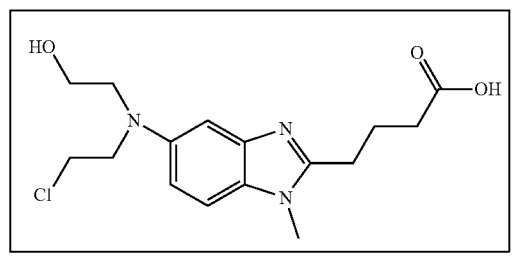 [SMILES: Cn1c(CCCC(=O)O)nc2cc(N(CCO)CCCl)ccc21]

As used herein the term "EE" or "Methyl Ester impurity" refers to Methyl 4-(5-(bis(2-chloroethyl)-amino)-1-methyl 1H-benzo[d]imidazol-2-yl) butanoate. The structure of EE is provided below:

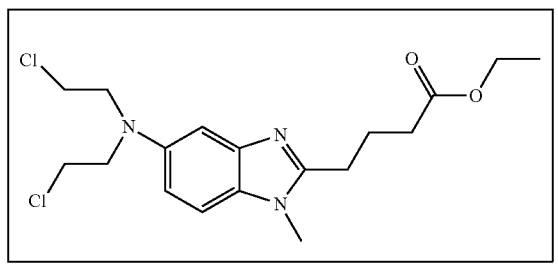 [SMILES: CCOC(=O)CCCc1nc2cc(N(CCCl)CCCl)ccc2n1C]

In accordance with the USP official monograph for polyethylene glycol, see USP35-NF30, the contents of which are incorporated by reference herein, the PEG pH is determined as follows: 5 g of PEG is dissolved into 100 mL carbon dioxide free water, and 0.3 mL of saturated KCl solution is added. The pH is then measured. This value is sometimes referred to as the apparent pH. Different amounts of organic or inorganic compounds can be added to the PEG in order to arrive at a pH of from about 6.0 to about 11. Preferably, the pH of the PEG is from about 6.0 to about 11. More preferably, the pH of the PEG is from about 9 to about 10. In other preferred aspects, the pH is about 10.

The pH of the PEG is not necessarily the same as the pH of the final bendamustine HCl formulation. Preferably, the pH of the final bendamustine-containing formulation is from about 2.0 to about 4. Preferably, the pH of the final bendamustine-containing formulation is about 2.7 to about 3.7. More preferably, the pH of the final bendamustine-containing formulation is about 3.5. The pH of the final bendamustine-containing formulation is measured in accordance with the USP <791> at 1:9 dilution of sample:water. Preferably, 10 mL aliquot of the final bendamustine containing formulation is added to 90 mL carbon dioxide free water. The pH is then measured and adjusted if necessary to the preferred range.

Without meaning to be bound by any theory or hypothesis, polyethylene glycol quality can vary from batch to batch, manufacturer to manufacturer, over product lifetime and as a result of handling. Such variation has made it difficult to make reproducible long-term storage stable bendamustine containing formulations with high amounts of polyethylene glycol, as the formation of PEG esters is high. In order to obtain reproducible formulations, PEG is treated with an organic or inorganic compound to achieve the desired pH. This treatment results in reproducible long-term storage stable bendamustine-containing compositions, with substantially no PEG ester formation.

In some aspects of the invention, organic compounds, inorganic compounds, and mixtures thereof are used to adjust pH of non-aqueous solvent(s). Organic compounds include carboxylic compounds, nitrogenous compounds, carbonates, bicarbonates, and salts thereof. Preferably, the organic compounds are selected from monoethanolamide, diethanolamine, ethylenediaminetetraacetic acid (EDTA) phospholipid salts, sodium sulfonic acid, sodium lauryl sulfate, quaternary amines, and quaternary ammonium salts. Preferably, the organic compounds are selected from inorganic salts of organic acids. More preferably, the organic compound is sodium acetate. Inorganic compounds include compounds known to those of skill in the art, including, but not limited to, salts of hydroxides and salts of phosphates, sodium formate, sodium phosphate, potassium hydroxide, and phosphoric acid. Most preferably, the inorganic compound is sodium hydroxide.

In some embodiments of the invention, the amount of the organic compound or inorganic compound functioning as the acidity/alkalinity adjustor is provided in an amount sufficient to obtain a pH of from about 6.0 to about 11 for the polyethylene glycol, as measured as per USP <791>.

In present invention, concentration of bendamustine hydrochloride in the inventive composition ranges from about 10 mg/mL to about 100 mg/mL, preferably 20 mg/mL to about 60 mg/mL, more preferably 25 mg/mL.

In an embodiment, the inventive compositions of the present invention may contain suitable pharmaceutically acceptable non-aqueous solvents, but not limited to alcohol, ethanol (for example, dehydrated alcohol or ethanol absolute), glycerine, butanediol, isopropanol, tetrahydrofuran (THF), polyethylene glycol ether, glycerol, dimethylacetamide, polyethylene glycol (e.g., polyethylene glycol 300, polyethylene glycol 400, polyethylene glycol 600), propylene glycol and mixtures thereof. For purposes of the present invention, the preferable pharmaceutically acceptable non-aqueous solvents are polyethylene glycol (PEG) or dehydrated alcohol or mixtures thereof.

Compositions of the present invention may additionally contain a preservative selected from the group consisting of benzoic acid and the sodium or potassium salts thereof, sorbic acid and the sodium or potassium salts thereof, chlorobutanol, benzyl alcohol, phenyl ethanol, methyl, ethyl, propyl or butyl-p-hydroxybenzoates, phenol, m-cresol, p-chloro-m-cresol, phenylmercury nitrate or benzalkonium chloride.

In an embodiment, the present invention provides a stable, antioxidant-free, ready-to-dilute, liquid composition comprising bendamustine, polyethylene glycol and dehydrated alcohol.

In another embodiment, the present invention provides a stable, antioxidant-free, ready-to-dilute liquid composition comprising bendamustine hydrochloride, mixture of polyethylene glycol in an amount of about 90% w/w and dehydrated alcohol in an amount of about 10% w/w, and sodium hydroxide.

In a further embodiment, the present invention provides a stable, ready-to-dilute liquid composition comprising bendamustine hydrochloride, mixture of polyethylene glycol in an amount of about 94% w/w and dehydrated alcohol in an amount of about 3.5% w/w, and sodium hydroxide, wherein the composition is free of antioxidant.

In a further embodiment, the present invention provides a stable, ready-to-dilute liquid composition comprising bendamustine hydrochloride, mixture of polyethylene glycol in an amount of about 95% w/w and dehydrated alcohol in an amount of about 4% w/w, and sodium hydroxide, wherein the composition is free of antioxidant.

In other embodiment, the present invention provides a stable, ready-to-dilute liquid composition comprising bendamustine hydrochloride, mixture of polyethylene glycol in an amount of about 99% w/w and dehydrated alcohol in an amount of about 1% w/w, and sodium hydroxide, wherein the composition is free of antioxidant.

In other embodiment, the present invention provides a stable, ready-to-dilute liquid composition comprising bendamustine hydrochloride, mixture of polyethylene glycol in an amount of about 99.5% and dehydrated alcohol in an amount of about 0.5%, and sodium hydroxide, wherein the composition is free of antioxidant.

In other embodiments of the invention, the pharmaceutically acceptable non-aqueous solvent is a mixture of PEG and dehydrated alcohol. The amount of PEG and dehydrated alcohol can also be varied within the ranges, i.e., the ratio of PEG:dehydrated alcohol in the pharmaceutically acceptable non-aqueous solvent can range from about 99.9:0.1 to about 50:50 (w/w), preferably 94:3.5 (w/w). In an embodiment of the present invention the polyethylene glycol has an average molecular weight ranging from about 100 to about 20,000, preferably from about 100 to about 10,000, more preferably from about 100 to about 1,000. In another embodiment of the present invention the polyethylene glycol has an average molecular weight of 400 (for example commercially available as Super Refined™ PEG-400).

In some embodiments, the inventive bendamustine hydrochloride containing compositions are administered as intravenous infusions at volumes of about 50 mL or about 250 mL or about 500 mL over a time period of about 10 minutes or about 20 minutes or about 60 minutes respectively.

In an embodiment, the inventive compositions of the present invention may be diluted with parenterally acceptable diluents such as water for injection (WFI), 0.9% saline (normal saline), 0.45% saline (half normal saline) or 2.5% dextrose/0.45% saline or 5% dextrose.

In an embodiment, sufficient amount of a concentrated, ready-to-dilute, liquid composition containing 25 mg/mL bendamustine hydrochloride can be transferred to a suitable fixed volume diluent container such as infusion bag containing 50, 100, 250 or 500 mL of parenterally acceptable diluents.

Preferably, the stable ready-to-use, antioxidant-free, compositions for human use will be provided in the form of a solution which is suitable for intravenous administration. The pharmaceutical compositions may be formulated according to conventional pharmaceutical practice. The compositions of the invention can be administered in any conventional manner. It will be readily appreciated by those skilled in the art how to administer compositions of the present invention to a human.

In an embodiment, the inventive stable, antioxidant-free, injectable ready-to-dilute liquid compositions suitable for parenteral administration comprises (a) therapeutically effective amount of bendamustine hydrochloride; (b) one or more pharmaceutically acceptable non-aqueous solvents; and (c) one or more pharmaceutically acceptable excipients.

In an embodiment, the present invention provides stable, antioxidant-free, ready-to-dilute liquid compositions suitable for parenteral administration comprises (a) bendamustine hydrochloride; (b) one or more pharmaceutical acceptable non-aqueous solvents selected from dehydrated alcohol (>99.2% v/v ethanol), ethanol absolute, glycerine, polyethylene glycol, dimethylacetamide, N-methyl-pyrrolidone, dimethyl sulfoxide, or suitable mixtures thereof; (c) at least one pH adjusting agent selected from sodium hydroxide, potassium hydroxide, magnesium hydroxide, sodium carbonate, tromethamine, sodium linoleate, sodium oleate, potassium carbonate, potassium linoleate, potassium oleate, and mixtures thereof and (d) optionally, one or more additional pharmaceutically acceptable excipients.

In an embodiment, the present invention provides stable, antioxidant-free, ready-to-dilute solutions suitable for parenteral administration comprises (a) bendamustine hydrochloride; (b) one or more pharmaceutical acceptable non-aqueous solvents; (c) at least one pH adjusting agent and (d) optionally, one or more additional pharmaceutically acceptable excipients, wherein the solution has a pH in the range of about 2 to about 5.

In an embodiment, the present invention provides stable, antioxidant-free, ready-to-dilute solutions suitable for parenteral administration comprises (a) bendamustine hydrochloride; (b) one or more pharmaceutical acceptable non-aqueous solvents; (c) optionally, at least one pH adjusting agent and (d) optionally, one or more additional pharmaceutically acceptable excipients, wherein the level of the total impurities resulting from the degradation of the bendamustine in the inventive compositions is less than about 5% as determined by HPLC at a wavelength of 235 nm after at least about 6 months at a temperature of from about 2-8° C. Preferably, the bendamustine-containing inventive compositions demonstrate long-term storage stability for at least about 6 months, especially when stored at the lower (refrigerated) temperatures.

In an embodiment, the present invention provides stable, antioxidant-free, ready-to-dilute solutions suitable for parenteral administration comprises (a) bendamustine hydrochloride; (b) polyethylene glycol 400; (c) dehydrated alcohol; (d) sodium hydroxide and (e) optionally, one or more additional pharmaceutically acceptable excipients.

The pharmaceutical compositions of the present invention may contain pH adjusting agents. The pH adjusting agents are selected from the group consisting of hydrochloric acid, sodium hydroxide, potassium hydroxide, magnesium hydroxide, sodium carbonate, tromethamine, sodium linoleate, sodium oleate, potassium carbonate, potassium linoleate, potassium oleate, and mixtures thereof. In one embodiment, pharmaceutical composition comprising bendamustine hydrochloride can be formulated at any suitable pH ranging from about 2 to about 5 when measured at room temperature.

In an embodiment, the present invention provides stable, antioxidant-free, ready-to-dilute solutions suitable for parenteral administration comprises a) bendamustine hydrochloride; b) one or more pharmaceutical acceptable non-aqueous solvents; c) an organic compound or inorganic compound, or mixtures thereof in an amount sufficient to obtain a pH of from about 6.0 to about 11 for the polyethylene glycol, as measured using USP monograph for polyethylene glycol.

In an embodiment, stable, antioxidant-free, ready-to-dilute solutions suitable for parenteral administration comprises a) bendamustine hydrochloride; b) a pharmaceutically acceptable non-aqueous solvent including polyethylene glycol and dehydrated alcohol; c) an organic compound or inorganic compound, or mixtures thereof in an amount sufficient to obtain a pH of from about 6.0 to about 10.5 for the polyethylene glycol, as measured using USP monograph for polyethylene glycol.

In an embodiment, stable, antioxidant-free, ready-to-dilute solutions suitable for parenteral administration comprises a) bendamustine hydrochloride; b) a pharmaceutically acceptable non-aqueous solvent including polyethylene glycol and dehydrated alcohol; c) an organic compound or inorganic compound, or mixtures thereof in an amount sufficient to obtain a pH of from about 6.0 to about 10.5 for the polyethylene glycol, as measured using USP monograph for polyethylene glycol.

In an embodiment, stable, antioxidant-free, ready-to-dilute solutions suitable for parenteral administration comprises a) bendamustine hydrochloride; b) a pharmaceutically acceptable non-aqueous solvent including polyethylene glycol and dehydrated alcohol; c) sodium hydroxide in an amount sufficient to obtain a pH of from about 6.0 to about 10.5 for the polyethylene glycol, as measured using USP monograph for polyethylene glycol.

In an embodiment, stable, antioxidant-free, ready-to-dilute solutions suitable for parenteral administration comprises a) bendamustine hydrochloride; b) 95% polyethylene glycol and 5% dehydrated alcohol; c) sodium hydroxide in an amount sufficient to obtain a pH of from about 6.0 to about 10.5 for the polyethylene glycol, as measured using USP monograph for polyethylene glycol.

In an embodiment, stable, antioxidant-free, ready-to-dilute solutions suitable for parenteral administration comprises a) bendamustine hydrochloride; b) a mixture of PEG and alcohol within the desired ratios ranging from about 99:1 to 50:50; c) an organic compound or inorganic compound, or mixtures thereof in an amount sufficient to obtain a pH of from about 6.0 to about 10.5 for the polyethylene glycol, as measured using USP monograph for polyethylene glycol.

In an embodiment, the present invention provides stable, antioxidant-free, ready-to-dilute solutions suitable for parenteral administration comprises a) bendamustine hydrochloride; b) one or more pharmaceutical acceptable non-aqueous solvents; c) an organic compound or inorganic compound, or mixtures thereof in an amount sufficient to obtain a pH ranging from about 2.7 to about 4.0 for the long-term storage stable bendamustine-containing solutions.

In an embodiment, the present invention provides stable, antioxidant-free, ready-to-dilute solutions suitable for parenteral administration comprises a) bendamustine hydrochloride; b) a mixture of PEG and alcohol c) sodium hydroxide in an amount sufficient to obtain a pH of from about 2.7 to about 4.0 for the long-term storage stable bendamustine-containing solutions.

In an embodiment, the present invention relates to a method of preparing an injectable composition comprising following steps: (i) neutralizing polyethylene glycol (PEG) to required pH using sodium hydroxide solution; (ii) adding dehydrated alcohol and bendamustine separately or simultaneously to neutralized polyethylene glycol (PEG) and stirring to form a clear bulk solution; (iii) optionally adjusting pH of bulk solution to required pH; (iv) purging the nitrogen gas throughout the procedure; (v) filtering the final solution; (vi) filling the final solution in vials and stoppering with stoppers.

In an embodiment, the present invention relates to a method of preparing an injectable composition comprising following steps: (i) neutralizing polyethylene glycol (PEG) to required pH using sodium hydroxide solution and purged with nitrogen to get dissolved oxygen is less than 2 ppm; (ii) adding one or more non-aqueous solvents and bendamustine separately or simultaneously to neutralized polyethylene glycol (PEG) and stirring to form a clear bulk solution; (iii) optionally adjusting pH of bulk solution to required pH; (iv) purging the nitrogen gas throughout the procedure; (v)

filtering the final solution; (vi) filling the final solution in vials and stoppering with stoppers.

A pharmaceutically inert gas may be bubbled into the solution to drive out oxygen, which may be selected from nitrogen or carbon dioxide. Preferably, the solution was kept under nitrogen, argon or carbon dioxide sparging until dissolved oxygen is less than 5 ppm, preferably less than 2 ppm in the final solution.

The compositions of the present invention can be packaged in any suitable sterile vial or container fit for the sterile storage of a pharmaceutical such as bendamustine. Containers suitable according to the present invention include, but not limited to, vials, cartridges, pre-filled syringes, auto-injectors, IV-infusion bags, bottles and ampoule presentations. Containers may be fabricated from glass or from polymeric materials. Suitable containers should be of a size sufficient to hold one or more doses of bendamustine hydrochloride.

The polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), teflon, nylon, acetal (Delrin), polymethylpentene, PVDC, ethylvinylacetate, AN-copolymer etc. In addition, cyclic olefin copolymer (COC), crystal zenith (CZ) resin containers and similar resins can be used in manufacturing vials and syringes.

In an embodiment, the present invention provides stable, antioxidant-free, injectable bendamustine solution in single-dose and/or multi-dose compositions. In some embodiments, the composition may be contained in vials or pre-filled syringes. In some embodiments, the vials may be made from clear glass, amber glass, or plastic. In some embodiments, the vials or pre-filled syringes may be in the range of about 0.1 mL to 100 mL in volume, preferably in the range of about 1 mL to 50 mL, more preferably in the range of about 1 mL to 10 mL, most preferably in the range of about 1 mL to 5 mL, and most preferably in the range of about 1 mL to 4 mL. In some embodiments, the 4 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days.

Stability: As used herein, the term "stable" is defined as no more than about 5% loss of bendamustine hydrochloride under typical commercial storage conditions. In certain embodiments, the compositions of the present invention will have no more than about 4% loss of bendamustine hydrochloride, no more than about 3% loss of bendamustine hydrochloride, no more than about 2% loss of bendamustine hydrochloride, more preferably, no more than about 1.5% loss of bendamustine hydrochloride, no more than about 1% loss of bendamustine hydrochloride, under typical commercial storage conditions. The composition retains at least about 95% of the potency of bendamustine hydrochloride after storing the composition at a temperature 2-8° C. for at least 6 months, for at least 12 months, for at least 18 months or for at least 24 months or for at least 32 months, or for at least 36 months. The composition retains at least about 95% of the potency of bendamustine hydrochloride after storing the composition at a storage condition i.e., 25° C./60% RH for at least 6 months, for at least 12 months, for at least 18 months or for at least 24 months or for at least 32 months, or for at least 36 months. In certain aspects, the term "stable" or "extended stability" refers to chemical stability, wherein not more than 5% w/w of total impurities, preferably not more than 2.5% w/w of total impurities, more preferably not more than 1% w/w of total impurities are formed on storage at accelerated conditions of stability at 2-8° C. or 25° C./60% RH for at least 3 months, at least 6 months, at least 9 months, at least 12 months, at least 15 months, at least 18 months, at least 21 months, at least 24 months, at least 30 months and at least 36 months.

The inventors of the present application have carried out several experiments in order to develop a bendamustine hydrochloride composition in the form of a solution, having an improved stability, without using antioxidant. The inventors of the present application also surprisingly found that it is not necessary to control the level of headspace oxygen in the container by purging with an inert gas. To simplify operations, the headspace oxygen in the container is substantially removed (i.e., approximately less than 18% v/v) by filling the vials in an inert environment, without requiring an additional step of purging with inert gas. Preferably, the level of headspace oxygen in the container is not controlled by purging of an inert gas, which simplifies the manufacture of the compositions.

In other aspects, if desired, the level of headspace oxygen in the container can be controlled by e.g., bubbling of nitrogen gas into the solution & purging nitrogen gas over head space.

The present invention overcomes the stability limitations of bendamustine solutions by controlling the level of dissolved oxygen content less than 2 ppm.

In certain embodiments, the headspace in the container includes oxygen in an amount of from about 0.5% v/v to about 18.0% v/v, or from about 0.5% v/v to about 17.0% v/v, or from about 0.5% v/v to about 16.0% v/v, or from about 0.5% v/v to about 15.0% v/v, or from about 0.5% v/v to about 14.0% v/v, or from about 0.5% v/v to about 13.0% v/v, or from about 0.5% v/v to about 12.0% v/v, or from about 0.5% v/v to about 11.0% v/v, or from about 0.5% v/v to about 10.0% v/v, or from about 0.5% v/v to about 9.0% v/v, or from about 0.5% v/v to about 8.0% v/v, or from about 0.5% v/v to about 7.0% v/v, or from about 0.5% v/v to about 6.0% v/v, or from about 0.5% v/v to about 5.0% v/v, or from about 0.5% v/v to about 4.0% v/v, or from about 0.5% v/v to about 3.5% v/v, from about 0.5% v/v to about 3.0% v/v, or from about 0.5% v/v to about 2.5% v/v, or from about 0.5% v/v to about 2.0% v/v, or from about 0.5% v/v to about 1.5% v/v, or from about 0.5% v/v to about 1.0% v/v, or in some cases from about 0.1% v/v to about 0.5% v/v, or from about 0.1% v/v to about 0.4% v/v, or from about 0.1% v/v to about 0.3% v/v, or from about 0.1% v/v to about 0.2% v/v. For the sake of clarity and the ease of discussion and measurement, these values are taken for the bendamustine composition at the time of its manufacture ("time zero" data point), or during and up to 1 month from time zero.

In certain embodiments, the invention relates to methods for making a liquid composition, comprising: (a) preparing a solution mixture comprising: (i) bendamustine hydrochloride, (ii) polyethylene glycol; (iii) dehydrated alcohol; and (iv) a pharmaceutically acceptable excipient; and (iv) less than 5% w/w total impurities, under conditions to maintain dissolved oxygen level of 2 parts per million (ppm) or less; and (b) filtering and filling a vial with the solution from (a) to produce the liquid composition.

In certain embodiments, the inventive stable, antioxidant-free, ready-to-use, liquid pharmaceutical composition comprises (a) bendamustine hydrochloride at concentration from about 10 mg/mL to about 100 mg/mL; (b) at least one pharmaceutically acceptable non-aqueous solvent; wherein the level of the total impurities resulting from the degradation of the bendamustine in the inventive compositions is less than about 5% as determined by HPLC at a wavelength of 235 nm after at least about 6 months at a temperature of from about 5° C. to about 25° C.

In certain embodiments, the inventive stable, antioxidant-free, ready-to-use, liquid pharmaceutical composition comprises (a) bendamustine hydrochloride at concentration from about 10 mg/mL to about 100 mg/ml; (b) at least one pharmaceutically acceptable non-aqueous solvent; wherein the level of the unknown impurities resulting from the degradation of the bendamustine in the inventive compositions is less than about 3% as determined by HPLC at a wavelength of 235 nm after at least about 6 months at a temperature of from about 2-8° C.

Dosage and administration: Bendamustine is used in the treatment of a number of cancers including chronic lymphocytic leukemias (CLL), Hodgkin's disease and multiple myelomas.

In an embodiment, a method of treating chronic lymphocytic leukemia or indolent B cell non-Hodgkin's lymphoma comprising parenterally administering to a subject a volume of about 500 mL or less of a liquid composition comprising: a) from about 0.05 to about 0.7 mg/ml of bendamustine; b) at least one non-aqueous solvent; c) a parenterally acceptable diluent; over a period of less than or equal to about 60 minutes; wherein the composition is antioxidant-free.

According to another embodiment, the present invention provides injectable bendamustine compositions at concentrations higher than 0.05 mg/mL after dilution in 50 mL or 100 mL or 250 mL or 500 mL parenterally acceptable diluents and methods of preparing such solutions. In particular, the present invention provides stable injectable bendamustine solutions at concentrations greater than or equal to 0.05 mg/ml and methods of preparing such solutions. In particular, the present invention provides stable aqueous bendamustine solutions for parenteral administration at concentrations about 0.05 mg/mL, about 0.06 mg/mL, about 0.07 mg/mL, about 0.08 mg/mL, about 0.09 mg/mL, about 0.1 mg/mL, about 0.2 mg/ml, about 0.3 mg/ml, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL about 4.9 mg/mL, about 5 mg/mL, about 5.1 mg/mL about 5.2 mg/mL, about 5.3 mg/mL, about 5.4 mg/mL, about 5.5 mg/mL, about 5.6 mg/mL, about 5.7 mg/mL, about 5.8 mg/mL about 5.9 mg/mL, about 6 mg/mL.

In an embodiment, a method for treating chronic lymphocytic leukemia or indolent B cell non-Hodgkin's lymphoma comprising parenterally administering to a subject a volume of about 250 mL or less of a liquid composition comprising: a) from about 0.2 to about 1.5 mg/mL of bendamustine; b) at least one non-aqueous solvent; c) a parenterally acceptable diluent; over a period of less than or equal to about 20 minutes; wherein the composition is antioxidant-free.

In an embodiment, a method for treating chronic lymphocytic leukemia or indolent B cell non-Hodgkin's lymphoma comprising parenterally administering to a subject a volume of about 250 mL or less of a liquid composition comprising: a) from about 0.05 mg/mL to about 1.36 mg/mL of bendamustine; b) at least one non-aqueous solvent; c) a parenterally acceptable diluent; over a period of less than or equal to about 20 minutes; wherein the composition is antioxidant-free.

In an embodiment, a method for treating chronic lymphocytic leukemia or indolent B cell non-Hodgkin's lymphoma comprising parenterally administering to a subject a volume of about 250 mL or less of a liquid composition comprising: a) from about 0.1 mg/mL to about 1.36 mg/mL of bendamustine; b) at least one non-aqueous solvent; c) a parenterally acceptable diluent; over a period of less than or equal to about 20 minutes; wherein the composition is antioxidant-free.

In an embodiment, a method for treating chronic lymphocytic leukemia or indolent B cell non-Hodgkin's lymphoma comprising parenterally administering to a subject a volume of about 50 mL or less of a liquid composition comprising: a) from about 0.49 to about 5.6 mg/mL of bendamustine; b) at least one non-aqueous solvent; c) a parenterally acceptable diluent; over a period of less than or equal to about 10 minutes; wherein the composition is antioxidant-free.

In an embodiment, a method for treating chronic lymphocytic leukemia or indolent B cell non-Hodgkin's lymphoma comprising parenterally administering to a subject a volume of about 250 mL or less of a ready-to-use liquid composition comprising: a) from about 0.2 to about 1.5 mg/ml of bendamustine; b) at least one non-aqueous solvent; c) a parenterally acceptable diluent; over a period of less than or equal to about 20 minutes.

In an embodiment, a method for treating chronic lymphocytic leukemia or indolent B cell non-Hodgkin's lymphoma comprising parenterally administering to a subject a volume of about 250 mL or less of a ready-to-use liquid composition comprising: a) from about 0.05 mg/mL to about 1.36 mg/mL of bendamustine; b) at least one non-aqueous solvent; c) a parenterally acceptable diluent; over a period of less than or equal to about 20 minutes.

In an embodiment, a method for treating chronic lymphocytic leukemia or indolent B cell non-Hodgkin's lymphoma comprising parenterally administering to a subject a volume of about 250 mL or less of a ready-to-use liquid composition comprising: a) from about 0.1 mg/mL to about 1.36 mg/ml of bendamustine; b) at least one non-aqueous solvent; c) a parenterally acceptable diluent; over a period of less than or equal to about 20 minutes.

In an embodiment, a method for treating chronic lymphocytic leukemia or indolent B cell non-Hodgkin's lymphoma comprising parenterally administering to a subject a volume of about 50 mL or less of a ready-to-use liquid composition comprising: a) from about 0.49 to about 5.6 mg/mL of bendamustine; b) at least one non-aqueous solvent; c) a parenterally acceptable diluent; over a period of less than or equal to about 10 minutes.

EXAMPLES

The following examples are provided for illustrative purpose only and should not be considered as limiting the scope of present invention in any way.

Preparation of 6N Sodium Hydroxide Solution:

24 grams of the sodium hydroxide was dissolved in 100 ml of water and stirred until clear solution was obtained.

Neutralization of PEG-400:

TABLE 1 pH of Neutralized PEG-400

| Quantity of 6N NaOH | Final pH of PEG-400 |
|---|---|
| 0 mL | 5.11 (Initial pH) |
| 1 mL | 9.13 |
| 1.15 mL | 9.35 |
| 1.45 mL | 9.57 |
| 1.95 mL | 10.05 |
| 2.1 mL | 10.19 |

Procedure to Measure pH of the PEG-400:

The pH of polyethylene glycol was determined in accordance with the USP official monograph for polyethylene glycol; see USP35-NF30, the contents of which are incorporated by reference herein. That is, 6N NaOH (in the amount shown in Table 1) was added drop by drop to 1700 grams of PEG-400 in a bottle. Then, 5 grams of the resulting PEG-400 composition withdrawn from the bottle and diluted with 100 mL of water. Next, 0.30 mL of saturated potassium chloride solution was added to produce a diluted PEG-400, and pH was measured by pH meter.

Analytical Methods Used for Samples Analysis:

The samples withdrawn from the compositions stored at condition (i.e., 2-8° C.) were analyzed for drug content using following HPLC procedure. Materials and general conditions are listed below:

TABLE 2

Chromatographic conditions

| | |
|---|---|
| Chromatographic Mode | Reverse phase Chromatography |
| Equipment | HPLC system equipped with UV detector |
| Column | Inertsil ODS 3 V, C-18, 150 × 4.6 mm, 5 µm or Inertsil ODS-2, C18, 150 × 4.6 mm, 5 µm |
| Materials & Reagents | 0.1% Trifluoroacetic acid (TFA) solution, HCL, Potassium dihydrogen phosphate, Water (Milli Q), Acetonitrile, Bendamustine HCL (Reference standard). |
| Wavelength | 235 nm |
| Flow rate | 1.5 mL/min |
| Injection volume | 20 µL |
| Column temperature | 25° C. |
| Sample temperature | 5° C. |
| Run time | 15 minutes |
| Retention time | 6 minutes |
| Buffer for Diluent | Accurately weigh 1.36 g of potassium dihydrogen phosphate in a 1000 mL volumetric flask, add 900 mL of MilliQ Water, sonicate to dissolve and bring up to volume with MilliQ Water. Adjust pH to 1.9 with diluted hydrochloric acid (1N or 2N). |
| Mobile Phase | Mix 700 mL of 0.1% TFA solution with 300 mL of Acetonitrile. |
| Diluent | Mix 700 mL of diluent buffer with 300 mL of Acetonitrile. Store the diluent at 2-8° C. diluent must have a temperature of 2-8° C. before use for the solutions preparation. |
| Mode of Elution | Isocratic |

The samples withdrawn from the compositions stored at condition (i.e., 2-8° C.) were analyzed for related substance determination using following HPLC procedure. Materials and general conditions are listed below:

TABLE 3

Chromatographic conditions

| | |
|---|---|
| Chromatographic Mode | Reverse phase Chromatography |
| Equipment | HPLC system equipped with UV detector |
| Column | Inertsil ® ODS 3 V, C-18, 150 × 4.6 mm, 5 µm |
| Materials & Reagents | 0.1% Trifluoroacetic acid (TFA) solution, HCL, Potassium dihydrogen phosphate, Water (Milli Q), Acetonitrile, Bendamustine HCL (Reference standard); Mono-chloro-impurity reference standard; Mono-substituted impurity reference standard. |
| Wavelength | 235 nm |
| Flow rate | 1.0 mL/min |
| Injection volume | 10 µL |
| Injector wash | Acetonitrile |
| Column temperature | 25° C. |
| Sample temperature | 5° C. |
| Run time | 60 minutes |
| Bendamustine Retention time | 24 minutes |
| Mobile Phase A | Mix 700 mL of 0.1% TFA solution with 300 mL of Acetonitrile. |
| Mobile Phase B | Acetonitrile |
| Diluent | Accurately weigh and transfer 1.36 g of potassium dihydrogen into 1000-mL MilliQ Water, sonicate until dissolution is completed and adjusted solution to pH 1.9 with diluted hydrochloric acid (1N or 2N). Mix the solution with acetonitrile at 70:30 ratio % v/v. Store diluent at 2-8° C. |

| | Gradient | | |
|---|---|---|---|
| | Time (minutes) | % Mobile Phase A | % Mobile Phase B |
| Mode of Elution | 0 | 95 | 5 |
| | 5 | 90 | 10 |
| | 20 | 70 | 30 |
| | 30 | 60 | 40 |
| | 40 | 40 | 60 |

TABLE 3-continued

| Chromatographic conditions | | |
|---|---|---|
| 45 | 30 | 70 |
| 50 | 50 | 50 |
| 55 | 95 | 5 |
| 60 | 95 | 5 |

Comparative Composition A

Comparative Composition A:

| Ingredients | Comparative Composition A mg/mL |
|---|---|
| Bendamustine HCl | 25.0 |
| Monothioglycerol | 5.0 |
| Dehydrated alcohol | 39.45 |
| Neutralised PEG-400 | q.s. to 1 mL |
| NaOH | q.s. to pH 9.0-10.5 |

TABLE 4

Stability results of Comparative Composition A

| | Comparative Composition A Condition 2-8° C. Storage duration | | |
|---|---|---|---|
| | Initial | 3 M | 6 M |
| pH | 3.1 | 3.2 | 3.2 |
| Assay (%) | 103.5 | 102.9 | 102.4 |
| Related Substances (% w/w) | | | |
| MS (RRT-0.62) | 0.03 | 0.11 | 0.12 |
| MC (RRT-0.67) | 0.09 | 0.06 | 0.16 |
| EE (RRT-1.21) | 0.05 | 0.04 | 0.06 |
| Max UI-1 | <0.02 | 0.06 | 0.06 |
| Total Impurities | 0.2 | 0.3 | 0.4 |

Example 1

Composition of Bendamustine Hydrochloride Injection 25 mg/mL

TABLE 5

Composition of bendamustine hydrochloride injection 25 mg/mL

| Ingredients | Composition A mg/mL | Composition B mg/mL |
|---|---|---|
| Bendamustine HCl | 25.0 | 25.0 |
| Dehydrated alcohol | 39.45 | 39.45 |
| Neutralised PEG-400 | q.s. to 1 mL | q.s. to 1 mL |
| Sodium Hydroxide content (mg/mL) | | |
| NaOH | 0.336 | 0.90 |
| pH parameters | | |
| Initial pH of PEG | 5.11 | 6.65 |
| pH of neutralised PEG | 10.19 | 9.5 |
| Final composition pH | 3.31 | 3.24 |

Manufacturing Procedure of Composition A:
1. Required quantity of neutralized PEG-400 (initial pH: 5.11) was taken in a glass beaker and purged with nitrogen to get the dissolved oxygen less than 2 ppm.
2. Specified quantity of dehydrated alcohol was added to neutralized PEG-400 and stirred continuously for 10 minutes to get clear solution.
3. Specified quantity of bendamustine hydrochloride was added to above solution under continuous stirring for 60 minutes to get final solution.
4. Final solution was filtered using 0.22 μm PVDF filter.
5. Final solution was filled in amber colour glass vials, blanket with nitrogen gas closed with Omniflex® plus rubber stoppers and crimp sealed.

TABLE 6

Stability results of Composition A

| | Composition A Condition 2-8° C. Storage duration | | | | |
|---|---|---|---|---|---|
| | Initial | 1 M | 2 M | 4 M | 6 M |
| pH | 3.38 | 3.39 | NP | NP | 3.41 |
| Head Space Oxygen (HSO) (% v/v) | 5 | 5.8 | 3.8 | 3.9 | 3.41 |
| Assay (%) | 101.4 | — | — | — | 102.4 |
| Related Substances (% w/w) | | | | | |
| MS (RRT-0.62) | 0.01 | 0.60 | 0.56 | 0.66 | 0.83 |
| MC (RRT-0.67) | 0.059 | 0.045 | 0.039 | 0.059 | 0.041 |
| EE (RRT-1.21) | ND | 0.009 | 0.012 | 0.03 | 0.041 |
| Max UI-1 | 0.021 | 0.034 | 0.009 | 0.018 | 0.08 |
| Total Impurities | 0.177 | 0.73 | 0.67 | 0.80 | 1.02 |

MS—Mono-substituted impurities;
MC—Mono-chloro impurities;
EE—Ethyl ester;
Max UI-1—Maximum Unknown impurity;
NP—Not performed;
HSO = Head Space Oxygen
* W = Weeks; M = Months Manufacturing Procedure of Composition B:
1. Required quantity of neutralized PEG-400 (initial pH: 6.65) was taken in a glass beaker and purged with nitrogen to get dissolved oxygen less than 2 ppm.
2. Specified quantity of dehydrated alcohol was added to neutralized PEG-400 and stirred continuously for 10 minutes to get clear solution.
3. Specified quantity of bendamustine hydrochloride was added to above solution under continuous stirring for 60 minutes to get final solution.
4. Final solution was filtered using 0.22 μm PVDF filter.
5. Final solution was filled in amber colour glass vials, blanket with nitrogen gas closed with OMNIFLEX® plus rubber stoppers and crimp sealed.

TABLE 7

Stability results of Composition B

| | Composition B Condition 2-8° C. Storage duration | | | | |
|---|---|---|---|---|---|
| | Initial | 1 M | 3 M | 4 M | 6 M |
| pH | 3.24 | NP | NP | 3.23 | 3.26 |
| Head Space Oxygen (HSO) (% v/v) | 11.70 | 15.3 | 11.2 | 7.0 | 5.8 |
| Assay (%) | 101.3 | NP | NP | 101.6 | 107.3 |
| Related Substances (% w/w) | | | | | |
| MS (RRT-0.62) | 0.03 | 0.09 | 0.26 | 0.26 | 0.68 |
| MC (RRT-0.67) | 0.073 | 0.126 | 0.059 | 0.044 | 0.047 |
| EE (RRT-1.21) | 0.002 | 0.009 | 0.025 | 0.028 | 0.054 |
| Max UI-1 | 0.030 | 0.011 | 0.039 | 0.033 | 0.038 |
| Total Impurities | 0.22 | 0.30 | 0.44 | 0.42 | 0.82 |

Example 2

Compositions of Bendamustine Hydrochloride Injection 25 mg/mL

TABLE 8

Compositions of bendamustine hydrochloride injection 25 mg/mL

| Ingredients | Composition | | | |
|---|---|---|---|---|
| | C | D | E | F |
| | mg/mL | | | |
| Bendamustine HCl | 25.00 | 25.00 | 25.00 | 25.00 |
| Dehydrated alcohol | 39.45 | 39.45 | 39.45 | 39.45 |
| Neutralised PEG-400 | q.s. to 1 ml | q.s. to 1 ml | — | q.s. to 1 ml |
| PEG-400 | | | q.s. to 1 ml | |
| Sodium hydroxide content (mg/mL) | | | | |
| Sodium hydroxide | 0.123 | 0.5004 | 0.492 | 0.5004 |
| pH Parameters | | | | |
| Initial pH of PEG | 6.65 | 6.7 | 6.65 | 6.65 |
| pH of Neutralised PEG | 9.43 | 10.5 | — | 10.7 |
| Final composition pH | 3.5 | 3.6 | 3.66 | 3.65 |

Manufacturing Procedure of Compositions C and F:
1. Required quantity of neutralized PEG-400 (initial pH of PEG: 6.65) was taken in a glass beaker and purged with nitrogen to get dissolved oxygen less than 2 ppm.
2. Specified quantity of bendamustine hydrochloride was added to above neutralized PEG-400 and stirred continuously for 35 minutes to get clear solution.
3. Specified quantity of dehydrated alcohol was added to above solution and stirred continuously for 10 minutes to get clear final solution.
4. Final solution was filtered using 0.22 μm PVDF filter.
5. 4.5 mL final solution was filled in 5 mL amber colour glass vials, blanket with nitrogen gas closed with Omniflex® plus rubber stoppers and crimp sealed.

Manufacturing Procedure of Composition D:
1. Required quantity of neutralized PEG-400 was taken in a glass beaker and purged with nitrogen to get dissolved oxygen less than 2 ppm.
2. Specified quantity of dehydrated alcohol was added to neutralized PEG-400 and stirred continuously for 10 minutes to get clear solution.
3. Specified quantity of bendamustine hydrochloride was added to above solution and stirred continuously for 60 minutes to get final solution.
4. Final solution was filtered using 0.22 μm PVDF filter.
5. 4.5 mL final solution was filled in 5 mL amber colour glass vials, blanket with nitrogen gas closed with Omniflex® plus rubber stoppers and crimp sealed.

Manufacturing Procedure of Composition E:
1. Required quantity of PEG-400 was taken in a glass beaker and purged with nitrogen to get dissolved oxygen less than 2 ppm.
2. Specified quantity of dehydrated alcohol was added to PEG-400 under continuous stirring for 10 minutes to get clear solution.
3. Specified quantity of bendamustine hydrochloride was added to above solution and stirred continuously for 35 minutes to get clear bulk solution.
4. pH of bulk solution was adjusted from 3.26 to 3.64 using 6N NaOH to obtain final solution.
5. Final solution was filtered using 0.22 μm PVDF filter.
6. 4.5 mL final solution was filled in 5 mL amber colour glass vials, blanket with nitrogen gas closed with Omniflex® plus rubber stoppers and crimp sealed.

TABLE 9

Stability results of Composition C

| | Composition C Condition 2-8° C. Storage duration | | | | |
|---|---|---|---|---|---|
| | Initial | 1 M | 2 M | 3 M | 6 M |
| pH | 3.5 | NP | NP | 3.41 | 3.42 |
| Head Space Oxygen (HSO) (% v/v) | NP | 8.70 | 5.70 | 5.60 | 0.15 |
| Assay (%) | 100.6 | NP | NP | 100.2 | NP |
| Related Substances (% w/w) | | | | | |
| MS (RRT-0.62) | ND | 0.44 | 0.57 | 0.53 | 0.77 |
| MC (RRT-0.67) | 0.031 | 0.063 | 0.088 | 0.060 | 0.073 |
| EE (RRT-1.21) | 0.003 | 0.007 | 0.02 | 0.019 | 0.042 |
| Max UI-1 | 0.026 | 0.067 | 0.046 | 0.016 | 0.041 |
| Total Impurities | 0.08 | 0.64 | 0.74 | 0.66 | 1.04 |

TABLE 10

Stability results of Composition D

| | Composition D Conditions 2-8° C. Storage duration | | |
|---|---|---|---|
| | Initial | 2 W | 1 M |
| pH | 3.5 | NP | |
| Related Substances (% w/w) | | | |
| MS (RRT-0.62) | 0.245 | 0.109 | 0.581 |
| MC (RRT-0.67) | 0.037 | 0.048 | 0.041 |
| EE (RRT-1.21) | <LOQ | 0.003 | 0.006 |
| Max UI-1 | 0.020 | 0.062 | 0.025 |
| Total Impurities | 0.307 | 0.287 | 0.743 |

TABLE 11

Stability results of Composition E

| | Composition E Condition 2-8° C. Storage duration | | | | |
|---|---|---|---|---|---|
| | Initial | 1 M | 2 M | 3 M | 6 M |
| pH | 3.66 | NP | 3.62 | 3.64 | 3.68 |
| Head Space Oxygen (HSO) (% v/v) | NP | 8.60 | 9.70 | 7.40 | 4.40 |
| Assay (%) | 103.6 | NP | 100.4 | 102.2 | 101.8 |
| Related Substances (% w/w) | | | | | |
| MS (RRT-0.62) | 0.04 | 0.11 | 0.43 | 0.52 | 0.78 |
| MC (RRT-0.67) | 0.047 | 0.055 | 0.056 | 0.106 | 0.041 |
| EE (RRT-1.21) | 0.003 | 0.008 | 0.013 | 0.016 | 0.037 |
| Max UI-1 | 0.019 | 0.027 | 0.02 | 0.02 | 0.042 |
| Total Impurities | 0.13 | 0.25 | 0.57 | 0.65 | 0.92 |

TABLE 12

Stability results of Composition F

| | Composition F Condition 2-8° C. Station | | |
|---|---|---|---|
| | Initial | 2 W | 1 M |
| pH | 3.65 | NP | NP |
| Related Substances (% w/w) | | | |
| MS (RRT-0.62) | 0.602 | 0.484 | 1.181 |
| MC (RRT-0.67) | 0.051 | 0.157 | 0.066 |
| EE (RRT-1.21) | 0.002 | 0.003 | 0.007 |
| Max UI-1 | 0.073 | 0.037 | 0.184 |
| Total Impurities | 0.760 | 0.712 | 1.470 |

Compositions D & F were precipitated after storing for 6 months at 25° C./60% RH.

Example 3

Dilution Compatibility (Admixture) Study of Bendamustine Hydrochloride Injection, 100 mg/4 mL (25 mg/mL) at 0.05 mg/mL and 1.36 mg/mL Dilution compatibility study of bendamustine hydrochloride injection, 100 mg/4 mL (25 mg/mL) were conducted at 0.05 mg/ml and 1.36 mg/ml to demonstrate the compatibility of drug product bendamustine hydrochloride injection, 100 mg/4 mL (25 mg/mL) presentation with the diluents (i.e., 0.9% NaCl Injection USP or 2.5% Dextrose/0.45% NaCl Injection USP) to be used for intravenous administration through the following tests like pH, description, assay of bendamustine, particulate matter & related substances. The following product composition was used for dilution compatibility studies.

TABLE 14

| Component | Concentration |
|---|---|
| Bendamustine HCl monohydrate USP | 25 mg/mL |
| Sodium Hydroxide NF* | q.s. |
| Dehydrated alcohol USP | 39.45 mg/mL@ |
| Polyethylene Glycol-400 USP | q.s. to 1.0 mL |

Dilution Solutions Preparation:

Dilution solutions will be prepared according to two different concentrations as per Table 15 below. Once diluted, the product solution will be analyzed at $T_0$ (initial), stored at room temperature (15-30° C. for 3 hours) and refrigerated temperature (2-8° C. for 24 hours) conditions and will be analyzed after the recommended time intervals.

TABLE 15

| Concentration 0.05 mg/mL | Concentration 1.36 mg/mL |
|---|---|
| Take 0.1 mL (0.1*25 mg = 2.5 mg) of drug product and transfer into diluent bag with 50 mL diluent (2.5 mg/50.1 mL = 0.0499 mg/mL~0.05 mg/mL). | Take 2.88 mL (2.88*25 mg = 72 mg) of drug product and transfer into diluent bag with 50 mL diluent (72 mg/52.88 mL = 1.3616 mg/mL) |

Bendamustine hydrochloride injection 100 mg/4 mL (25 mg/mL) will be diluted into appropriate diluents as reported in the table below:

TABLE 16

Storage conditions and sampling points for bendamustine hydrochloride injection 100 mg/4 mL (25 mg/mL) dilution solutions.

| Dilution Compatibility Mixtures | | | |
|---|---|---|---|
| Diluent | Diluted Bendamustine Concentration (mg/mL) | Storage Concentration | Sampling time points |
| 0.9% NaCl Injection USP | 0.05 | Room Temperature (15-30° C.) | 0 (Initial) and 3 hours |
| 0.9% NaCl Injection USP | 0.05 | Refrigerated Temperature (2-8° C.) | 0 (Initial) and 24 hours |
| 0.9% NaCl Injection USP | 1.36 | Room Temperature (15-30° C.) | 0 (Initial) and 3 hours |
| 0.9% NaCl Injection USP | 1.36 | Refrigerated Temperature (2-8° C.) | 0 (Initial) and 24 hours |

TABLE 17

| Dilution Compatibility Mixtures | | | |
|---|---|---|---|
| Diluent | Diluted Bendamustine Concentration (mg/mL) | Storage Concentration | Sampling time points |
| 2.5% Dextrose/0.45% Sodium Chloride Injection USP | 0.05 | Room Temperature (15-30° C.) | 0 (Initial) and 3 hours |
| 2.5% Dextrose/0.45% Sodium Chloride Injection USP | 0.05 | Refrigerated Temperature (2-8° C.) | 0 (Initial) and 24 hours |

TABLE 17-continued

Dilution Compatibility Mixtures

| Diluent | Diluted Bendamustine Concentration (mg/mL) | Storage Concentration | Sampling time points |
|---|---|---|---|
| 2.5% Dextrose/0.45% Sodium Chloride Injection USP | 1.36 | Room Temperature (15-30° C.) | 0 (Initial) and 3 hours |
| 2.5% Dextrose/0.45% Sodium Chloride Injection USP | 1.36 | Refrigerated Temperature (2-8° C.) | 0 (Initial) and 24 hours |

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

What is claimed:

1. A method of treating chronic lymphocytic leukemia or indolent B cell non-Hodgkin's lymphoma comprising administering to a patient in need thereof a therapeutically effective amount of a liquid composition consisting of:
   a) about 25 mg/mL of bendamustine or a pharmaceutically acceptable salt thereof;
   b) at least one non-aqueous solvent consisting of ethanol, glycerine, polyethylene glycol (PEG), propylene glycol, dimethylacetamide, N-methyl-pyrrolidone, or mixtures thereof; and
   c) optionally, a pH adjuster;
   wherein a level of total impurities in said liquid composition is not more than 5% w/w when stored at a temperature from about 2° C. to about 8° C. for 6 months as measured by HPLC;
   wherein said liquid composition is diluted with a parenterally acceptable diluent prior to administration to provide a diluted liquid composition; and
   wherein the liquid composition and the diluted liquid composition are antioxidant-free.

2. The method according to claim 1, wherein the liquid composition has a pH ranging from about 3.0 to about 5.0.

3. The method according to claim 1, wherein the liquid composition has a pH ranging from about 2.0 to about 5.0.

4. The method according to claim 1, wherein the liquid composition has a pH ranging from about 2.7 to about 3.7.

5. The method according to claim 1, wherein the polyethylene glycol (PEG) is PEG-400.

6. The method according to claim 1, wherein the ethanol is a dehydrated ethanol.

7. The method according to claim 1, wherein the bendamustine or a pharmaceutically acceptable salt thereof is bendamustine hydrochloride.

8. The method according to claim 1, wherein the at least one non-aqueous solvent contains a mixture of ethanol and polyethylene glycol (PEG).

9. The method according to claim 8, wherein the at least one non-aqueous solvent contains about 2-25% w/w of the ethanol and about 75-98% w/w of the polyethylene glycol.

10. The method according to claim 8, wherein the at least one non-aqueous solvent contains about 2-5% w/w of the ethanol and about 90-98% w/w of the polyethylene glycol.

11. The method according to claim 1, wherein the at least one non-aqueous solvent contains 39.45 mg/mL of ethanol.

12. The method according to claim 1, further comprising a pH adjuster selected from the group consisting of sodium hydroxide, potassium hydroxide, magnesium hydroxide, sodium carbonate, tromethamine, sodium linoleate, sodium oleate, potassium carbonate, potassium linoleate, potassium oleate, and mixtures thereof.

13. The method according to claim 1, wherein a level of ethyl ester impurity in said liquid composition is not more than 0.5% w/w when stored at a temperature from about 2° C. to about 8° C. for 6 months as measured by HPLC.

14. The method according to claim 1, wherein a level of mono-substituted impurity in said composition is not more than 3.5% w/w when stored at a temperature from about 2° C. to about 8° C. for 6 months as measured by HPLC.

15. The method according to claim 1, wherein the patient in need thereof is treated for chronic lymphocytic leukemia.

16. The method according to claim 1, wherein the patient in need thereof is treated for indolent B cell non-Hodgkin's lymphoma.

* * * * *